(12) United States Patent
Johnson et al.

(10) Patent No.: US 7,509,836 B2
(45) Date of Patent: Mar. 31, 2009

(54) GAS FLUX SYSTEM CHAMBER DESIGN AND POSITIONING METHOD

(75) Inventors: Mark A. Johnson, Hickman, NE (US); Andrew G. Ragatz, Lincoln, NE (US); Rex A. Peterson, Lincoln, NE (US)

(73) Assignee: LI-COR, Inc., Lincoln, NE (US)

( * ) Notice: Subject to any disclaimer, the term of this patent is extended or adjusted under 35 U.S.C. 154(b) by 268 days.

(21) Appl. No.: 11/217,922

(22) Filed: Sep. 1, 2005

(65) Prior Publication Data

US 2007/0044538 A1    Mar. 1, 2007

(51) Int. Cl.
*G01N 33/24* (2006.01)
(52) U.S. Cl. .................................. 73/19.01; 73/863.21
(58) Field of Classification Search ........................ None
See application file for complete search history.

(56) References Cited

U.S. PATENT DOCUMENTS

| | | | | |
|---|---|---|---|---|
| 4,444,041 | A * | 4/1984 | Zison | 73/19.04 |
| 5,355,739 | A * | 10/1994 | Cooper et al. | 73/864.73 |
| 5,394,949 | A * | 3/1995 | Wright et al. | 175/20 |
| 6,598,458 | B1 | 7/2003 | Edwards et al. | |
| 6,692,970 | B2 | 2/2004 | Butnor et al. | |
| 6,843,082 | B2 | 1/2005 | Vickers | |
| 2002/0000226 | A1 | 1/2002 | Butnor et al. | |
| 2002/0100860 | A1 | 8/2002 | Wieder | |
| 2006/0117840 | A1* | 6/2006 | Furtaw et al. | 73/149 |
| 2007/0144276 | A1* | 6/2007 | Johnson | 73/864.51 |

OTHER PUBLICATIONS

G.L. Hutchinson and G.P. Livingston, "Vents and seals in non-steady-state chambers used for measuring gas exchange between soil and the atmosphere", European Journal of Soil Science, vol. 52, pp. 675-682 (2001).

J.M. Welles, T.H. Demetriades-Shah and D.K. McDermitt, "Considerations for measuring ground CO2 effluxes with chambers," Chemical Geology, vol. 177, pp. 3-13 (2000).

F. Conen and K.A. Smith, "A re-examination of closed flux chamber methods for the measurement of trace gas emissions from soils to the atmosphere," European Journal of Soil Science, vol. 49, pp. 701-707 (1998).

N.T. Edwards, "A moving chamber design for measuring soil respiration rates," Oikos, vol. 25, pp. 97-101 (1974).

B.A. Kimball, "Canopy gas exchange: Gas exchange with soil," Limitations to efficient water use in crop production published by ASA-CSSA-SSSA, pp. 215-226 (1983).

(Continued)

*Primary Examiner*—Hezron Williams
*Assistant Examiner*—Rose M Miller
(74) *Attorney, Agent, or Firm*—Townsend and Townsend and Crew LLP

(57) ABSTRACT

A gas flux chamber assembly with a soil collar and a chamber is provided. The chamber is moved between first and second positions, wherein the chamber is positioned on the soil collar in the first position and is positioned outside of an area above the soil collar in the second position. In operation, the chamber is first lifted off of the soil collar and is then rotated, about a rotational axis substantially parallel to the soil collar axis, outside of the area above the soil collar. These acts are reversed to move the chamber from the second position to the first position.

41 Claims, 6 Drawing Sheets

OTHER PUBLICATIONS

"SRS-1000 Portable Soil Respiration System," ADC BioScientific Ltd., 2 pages (Oct. 2003).

"S.O.A.P. Static Outside Air Probe," Air Monitor Corporation, 2 pages (May 2000).

"Static Pressure Reference Probe for Outdoor Use," Micatrone, 2 pages (2002).

"SPH10/20 Static Pressure Heads for Minimizing Wind Induced Error," Vaisala, 2 pages (2003-2004).

"Meteorological Measurement Systems," Paroscientific, Inc., 2 pages (2001).

"Design and Characteristics of the MET3A High-Performance Dual Pressure Port," Paroscientific, Inc., 5 pages (2000).

"MET3A Meteorological Measurement System," Paroscientific, Inc., 2 pages (1999).

"Model 61002 Gill Pressure Port," R.M. Young Company, 1 page (2000).

"Model 61202 Barometric Pressure Sensor," R.M. Young Company, 1 page (2004).

"The 6400-09: Soil $CO_2$ Flux Chamber," LI-COR Bioscience, 2 pages (1997).

"LI-8100 Automated Soil $CO_2$ Flux System," LI-COR Bioscience, 8 pages (Dec. 8, 2003).

Photograph of the LI-8100 Survery Chamber, 1 page, shown Oct. and Nov. 2003.

Photograph of the LI-8100 Long-Term Chamber, 1 page, shown Dec. 8, 2003.

"The Impact of Pressure Perturbation on Chamber-Based Soil $CO_2$ Efflux Measurement," Xu et al., 1 page, presented at American Geophysical Union meeting Dec. 7, 2004.

U.S. Appl. No. 11/063,955, "Pressure Vent, Leak Detection, and Kinetic Volume Determination Methods and Systems," inventors: Michael D. Furtaw, Dayle K. McDermitt, and Liukang Xu, filed Feb. 22, 2005.

Automated Monitoring of Soil Respiration: A Moving Chamber Design, Nelson T. Edwards and Jeffrey S. Riggs, p. 1266-1271, (2003).

Dynamax, Soil Respiration Chamber SRC-MV5, 1 page, (2003).

PP Systems Data Sheet, SRC-1 Soil $CO_2$ Flux System, "A closed system for accurate measurement of soil $CO_2$ flux;" Feb. 18, 2005, 2 pages.

PP Systems Data Sheet, CFX-2 Soil $CO_2$ Flux System, "An open system for accurate measurement of soil $CO_2$ flux;" Apr. 4, 2005, 2 pages.

Westsystems, Continuous Monitoring Station, http://www.westsystems.com/cm_fixed_station.html; Aug. 15, 2005, 3 pages.

West Systems Portable soil flux meter, http://www.westsystems.com/documentation/SoilFluxPortableBrochure0503.pdf; 2 pages, no date.

Soil CO2 Flux System, Soil CO2 Chamber snapshots, http://www.insituflux.org/CO2Chambersnapshots.html; Printed Aug. 15, 2005, 2 pages.

Soil CO2 Flux System, System snapshots, http://www.insituflux.org/systemksnapshots.html; Printed Aug. 15, 2005, 1 page.

Automated Carbon Efflux System Patented, SRS Researchers Patent Automated Carbon Efflux System, http://www.srs.fs.usda.gov/about/newsrelease/nr_2004-02-25-butnor.htm; Feb. 25, 2004, 2 pages.

Automatic Carbon Efflux System, A.C.E.S.—USDA Forest Service SRS-4154, The Automatic Carbon Efflux System (A.C.E.S.), http://www.srs.fs.usda.gove/soils/research/aces.html; Jul. 7, 2003, 4 pages.

\* cited by examiner

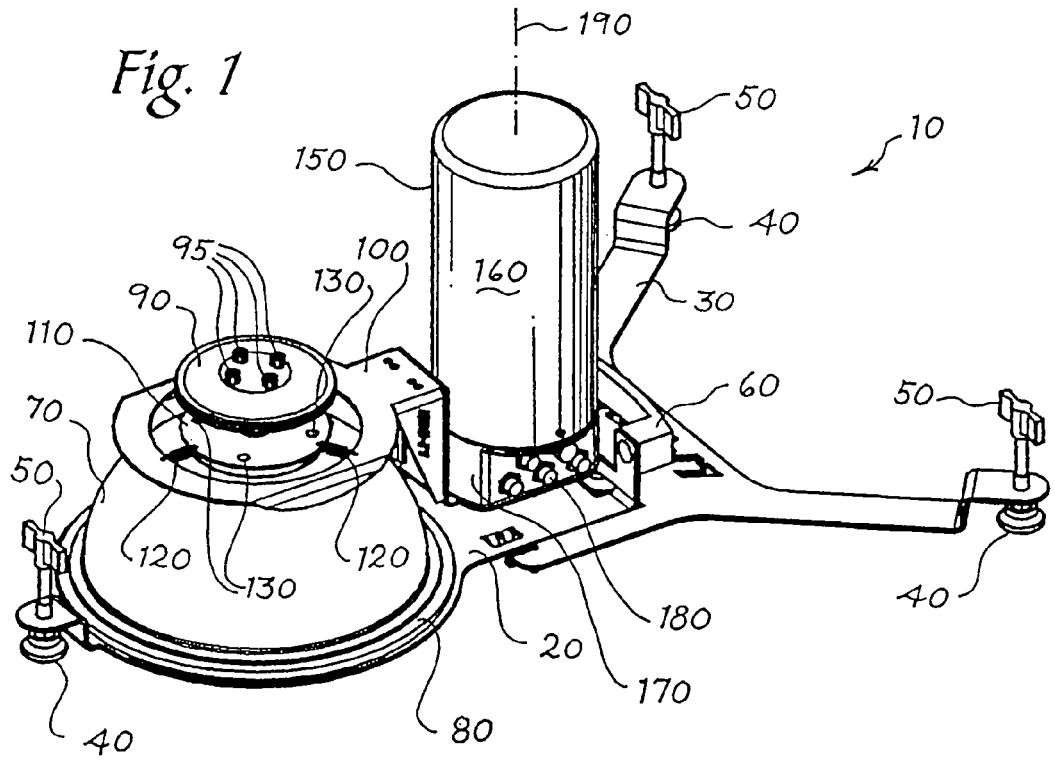
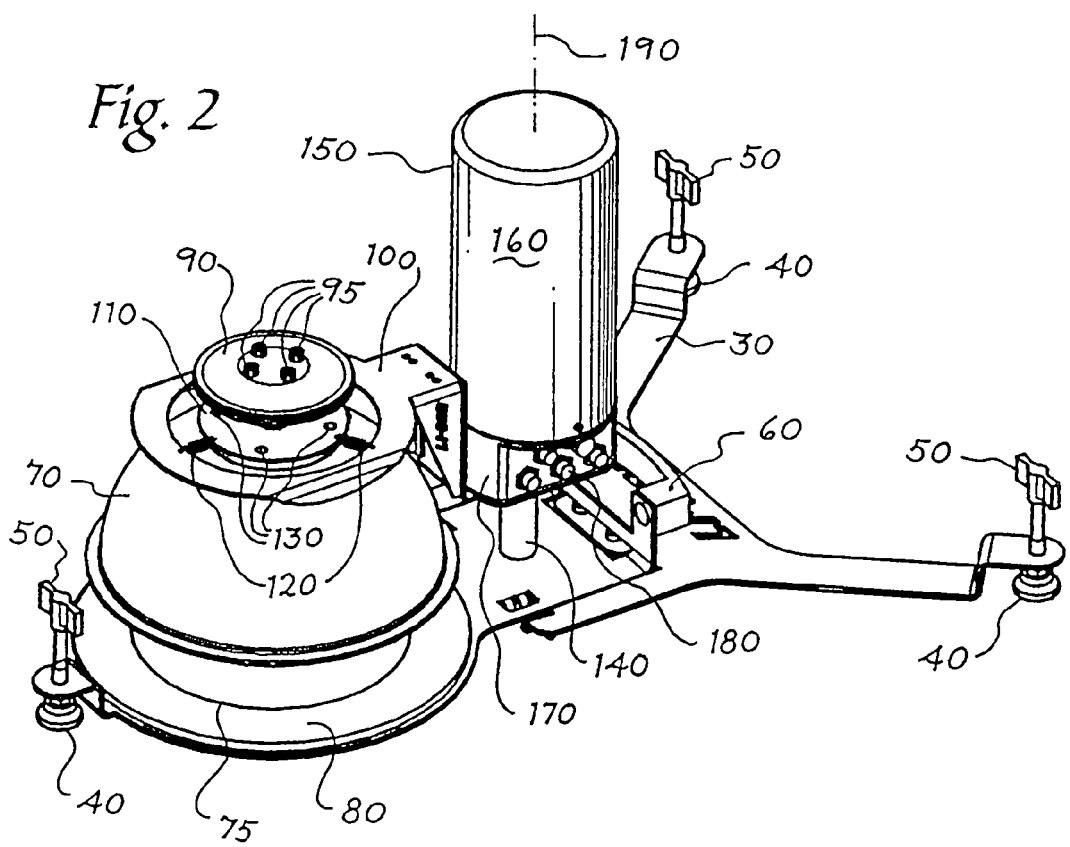

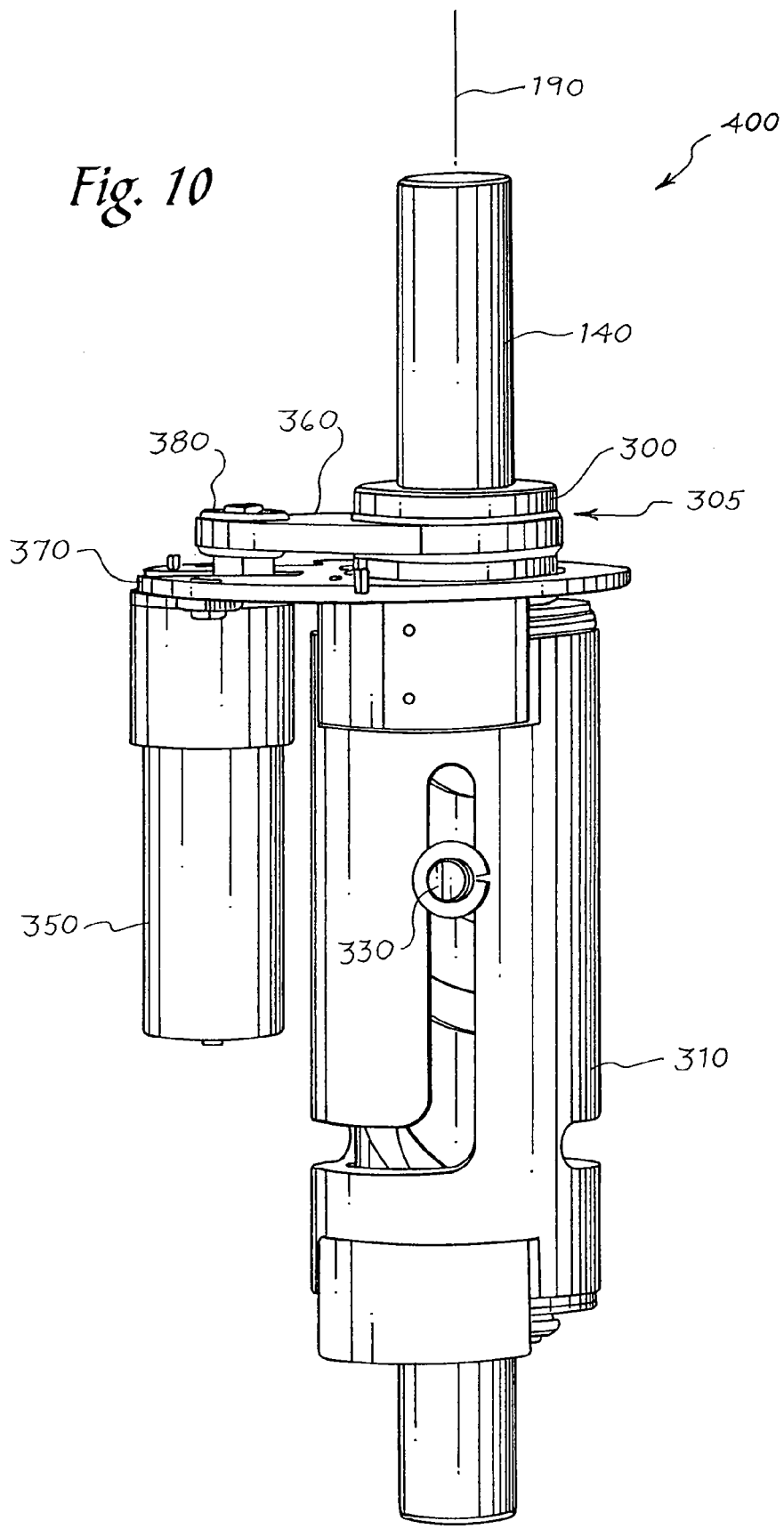

GAS FLUX SYSTEM CHAMBER DESIGN AND POSITIONING METHOD

BACKGROUND

Gas flux chamber assemblies are used to measure trace gas emissions (e.g., $CO_2$ and methane) from soils. One such assembly is the LI-8100 Long-Term Chamber by LI-COR Biosciences. The LI-8100 Long-Term Chamber is electrically actuated via a geared, motorized chain drive mechanism to move a chamber between two positions—one over the soil sampling area and another away from the soil sampling area. Trace gas emissions are measured when the chamber is over the soil sampling area. When measurements are not being taken, the chamber is moved away from the sampling area to expose the soil to the environment, thereby allowing environmental factors (e.g., wind, rain, sun, etc.) to reach the soil just as it would if the chamber were not present. This allows a researcher to measure soil $CO_2$ flux in as representative an environment as possible, thereby ensuring maximum yield from the sample area.

The LI-8100 Long-Term Chamber uses a strut mechanism to move the chamber through a seven-inch radius vertical circular arc over and away from the sampling area. The strut mechanism maintains the chamber opening downward to avoid collection of precipitation and debris while in the open or moving state. The unique advantage of the LI-8100 Long-Term Chamber as compared to other chamber designs is the ability to move the chamber clear from the sampling area, which is important for long-term unattended measurements. An unobstructed sampling area allows natural exposure to sunlight, shading, precipitation, and temperature effects, thereby minimizing the influence of the testing equipment on the measured gas flux. In contrast, assemblies that simply move a chamber directly above the sampling area can shade the sampling area with the chamber, thereby creating an artificial condition that can influence the flux measurements. Also, in systems where the chamber is stationary and a movable chamber lid covers and uncovers the chamber, the chamber itself protrudes from the soil surface even when a measurement is not being taken and obstructs the sampling area.

SUMMARY

The present invention is defined by the following claims, and nothing in this section should be taken as a limitation on those claims.

By way of introduction, in one preferred embodiment, a gas flux chamber assembly is provided comprising a soil collar and a chamber. The chamber is moved between first and second positions, wherein the chamber is positioned on the soil collar in the first position and is positioned outside of an area above the soil collar in the second position. In operation, the chamber is first lifted off of the soil collar and is then rotated, about a rotational axis substantially parallel to the soil collar axis, outside of the area above the soil collar. These acts are reversed to move the chamber from the second position to the first position. Other preferred embodiments are provided, and each of the preferred embodiments described herein can be used alone or in combination with one another.

The preferred embodiments will now be described with reference to the attached drawings.

BRIEF DESCRIPTION OF THE DRAWINGS

FIG. 1 is an illustration of a gas flux chamber assembly of a preferred embodiment in which a chamber is in a first, closed/sampling position.

FIG. 2 is an illustration of a gas flux chamber assembly of a preferred embodiment in which a chamber is in a raised, lift position.

FIG. 10 is an illustration of a drive column assembly with a motor and belt of a preferred embodiment.

DETAILED DESCRIPTION OF THE PRESENTLY PREFERRED EMBODIMENTS

Figure 3:
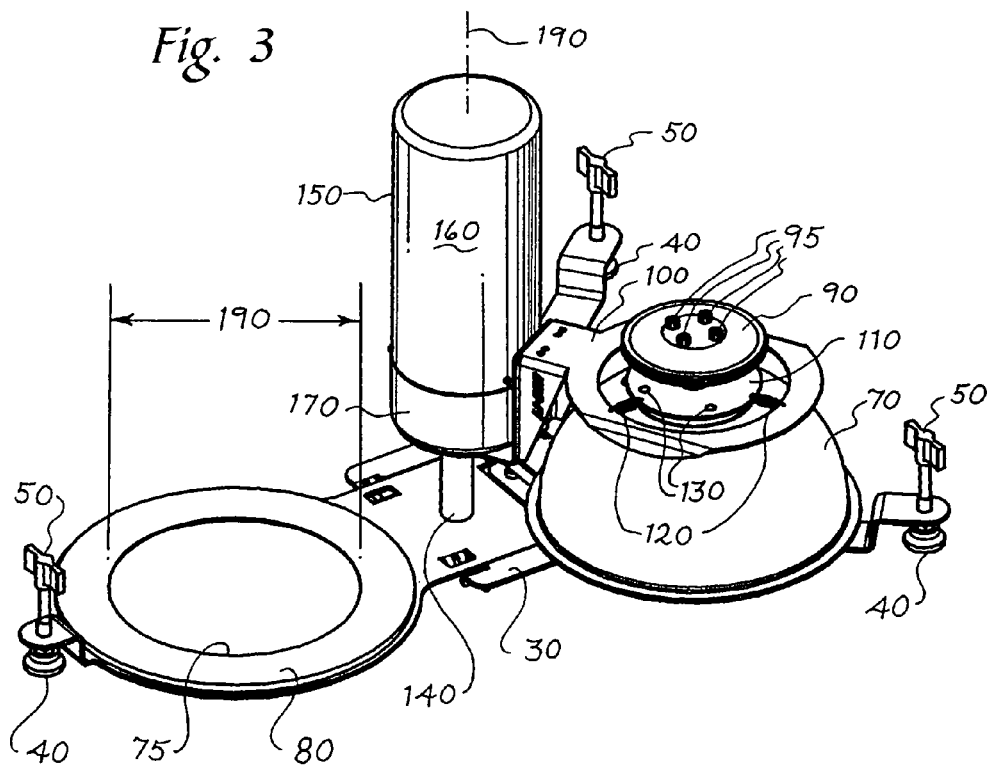
FIG. 3 is an illustration of a gas flux chamber assembly of a preferred embodiment in which a chamber is in a second, fully open/rotate position.

By way of introduction, the preferred embodiments presented herein describe a gas flux chamber with a lift-and-rotate method to move a sampling chamber to and from a monitoring area. The rigid sampling volume provides for true constant-volume measurements. When sampling is completed, the method first lifts the sampling chamber off of a soil collar and then rotates the chamber completely free of the sampling area. This exposes the sampling area to natural wind, precipitation, temperature, and sunlight. The exposure of the sampling area provides minimal disturbance of the soil microclimate, allowing long-term unattended measurements. When a measurement is commanded, the chamber is again rotated directly above the sampling area and gently lowered onto the sampling collar. While this lift-and-rotate can be performed with any suitable lift-and-rotate mechanism, one of the preferred embodiments presented herein describes a mechanism that produces the lift-and-rotate motion with a minimum of moving parts. Further, the entire operating mechanism in this preferred embodiment is enclosed in a sealed cylindrical column that requires no periodic maintenance. The simplicity of this preferred lift-and-rotate mechanism allows a smaller mechanism footprint, reduces complexity, and reduces cost. Further, these preferred embodiments replicate the advantages of the LI-COR LI-8100 Long-Term Chamber through a much simpler and more compact motion.

Turning now to the drawings, FIG. 1 is an illustration of a chamber assembly 10 of a preferred embodiment. The assembly 10 comprises a base 20 coupled with support legs 30. As used herein, the phrase "coupled with" means directly coupled with or indirectly coupled with through one or more components (named or unnamed herein). The support legs 30 comprises a plurality of feet 40 and thumbscrews 50 for adjusting the height of the feet 40 so the feet 40 rest on the ground. These components help ensure a stable, non-moving position when the assembly 10 is installed in a sample area. The adjustable support legs also introduce a three-point leveling mechanism for the chamber assembly 10 such that the chamber assembly 10 can be leveled with respect to the soil collar 75. The base 20 comprises a handle 60, which allows the chamber assembly 10 to be hand-carried and deployed in any desired location.

The assembly 10 also comprises a chamber 70. In FIG. 1, the chamber 70 is shown in a first position on a soil collar 75 that is embedded in soil to be observed (the soil collar is not shown in FIG. 1 but is shown in FIGS. 2 and 3). The soil collar 75 preferably has a minimal protrusion above the soil surface to minimize the impedance to sunlight, wind, precipitation and other exposure to the sampling area. A collar seal 80 coupled with base 20 is a gasket that helps form a gas-tight seal between the chamber 70 and the soil collar 75 and causes flux of trace gas emissions from the soil to move in a vertical direction. Preferably, the height of protrusion of the soil collar 75 above the soil surface is the thickness of the collar seal 80, which in a presently preferred embodiment, is less than 0.5 inches.

The assembly also comprises a vent 90 coupled with the chamber 70. The vent has four thumbscrews 95 for disassembling the vent 90 for cleaning. The vent 90 maintains the ambient soil surface pressure within the chamber 70 by compensating for the effect of wind on the air pressure at the soil surface. U.S. patent application Ser. No. 11/063,955, which is assigned to the assignee of the present invention and is hereby incorporated by reference, describes a presently preferred vent.

The chamber 70 is coupled with a support structure 100 via a spring disk 110 and three extension springs 120 oriented horizontally. The spring disk 110 is attached to the chamber 70 with screws 130 in this preferred embodiment, and the springs 120 support the chamber 70 radially around the circumference of the ring on one end of the support structure 100. Accordingly, the chamber support structure 100 is compliantly coupled to the chamber 70 through the three extension springs 120. An analogous design can be seen in consumer trampolines, in which an inextensible fabric is horizontally supported by extension springs around its periphery. The extension springs 120 allow the chamber 70 to "float" so that exact parallelism between the chamber support structure 100 and the collar seal 80 is not required. Moreover, through appropriate choice of spring rates, the downward force on the chamber 70 can be made a weak function of the position of the chamber support structure 100. This allows the chamber support structure 100 to be coarsely positioned by the lift-and-rotate mechanism without having a significant impact on the magnitude of the sealing force between the chamber 70 and the collar seal 80. This avoids the cost and complexity of designing a constant-force mechanism to maintain a constant sealing force between the chamber 70 and collar seal 80. A simpler and cheaper kinematic positioning mechanism is implemented along with a compliant structure that applies nearly the same force regardless of kinematic imperfections (e.g., dimensional tolerances, relaxation of gasketing mateterials, variations in assembled dimensions, etc.) In a presently preferred embodiment, the extension springs 120 have a spring constant of 19 lbs/inch and are stainless steel. A suitable spring is part number 80404S from Century Spring.

The other end of the support structure 100 is coupled with an outer column 310. The outer column 310 is not shown in FIG. 1, as it is contained in the enclosure 150 when the chamber 70 is in the first position, but will be described below with respect to FIGS. 2 and 3. In this preferred embodiment, the enclosure 150 contains a lift-and-rotate mechanism, which will be described below. The outer column 310 forms one component of the lift-and-rotate mechanism of this preferred embodiment. The enclosure 150 contains a top half 160 shaped like an inverted can and a bottom half 170 with electrical connectors 180 for controlling the movement of the chamber 70 and for connecting soil temperature probe(s), soil moisture probe(s), and a power supply. In a presently preferred embodiment, the top half of the enclosure 160 is a deep-drawn aluminum can that is powder coated to make it robust to weather and mechanical abuse, and the bottom half 170 is cast aluminum and powder coated.

In this preferred embodiment, the lift-and-rotate mechanism moves the chamber 70 between a first position, in which the chamber 70 is positioned on the soil collar, to a second position, in which the chamber 70 is positioned outside of an area above the soil collar. This movement is shown in FIGS. 1-3. In FIG. 1, the chamber 70 is in the first position, which will also be referred to herein as the closed or sampling position. The soil sampling area is directly beneath the hemispherical chamber 70. It is in this first position that a gas analyzer (not shown) coupled with the chamber 70 with gas inlet and outlet conduits (not shown) measures the change in concentration over time of a gas leaving or entering the soil, which indicates the flux rate of the gas moving from/to the soil to/from the atmosphere. When the measurement is complete, the lift-and-rotate mechanism moves the chamber 70 from the first position to the second position by lifting the chamber 70 vertically off of the soil collar 75 (shown in FIG. 2).

As shown in FIG. 2, the radius of the soil collar 75 is smaller than the radius of the chamber 70 in this embodiment, and the collar seal 80 seals the connection between the chamber 70 and the soil collar 75. Accordingly, in this embodiment, the chamber 70 is "on" the soil collar 75 when the chamber 70 is on the collar seal 80. In other embodiments where the radius of the soil collar 75 more closely matches the radius of the chamber 70, the chamber 70 is "on" the soil collar 75 when the chamber 70 directly contacts the soil collar 75. Accordingly, the phrase "on the soil collar" as used in the claims should be interpreted to cover implementations where the chamber is directly on the soil collar or indirectly on the soil collar though the use of a collar seal or some other intermediary component.

Preferably, the chamber 70 is lifted only as high as necessary to clear the protrusion of the soil collar 75. Once the chamber 70 has been lifted sufficiently clear of the soil collar 75, the lift-and-rotate mechanism rotates the chamber 70 about a vertical rotational axis 190 of the lift-and-rotate mechanism outside of the area 190 above the soil collar 75, completely clear of the sampling area (see FIG. 3). The vertical rotational axis 190 is substantially parallel to the soil collar 75 (depending on ground conditions and the installation of the soil collar 75, the soil collar 75 may not be exactly parallel to the vertical rotational axis 190). The orientation of the chamber 70 is maintained in a downward facing direction to avoid the accumulation of precipitation and/or debris. In addition to avoiding the accumulation of precipitation and/or debris, the downward orientation avoids the creation of a bluff body. During windy conditions, the soil chamber can act as a sail on the assembly and cause the entire assembly to vibrate, shift, and potentially tip. Maintaining the chamber in a downward orientation keeps the assembly 10 more stable in windy conditions. In contrast, a clamshell design, in which the chamber or chamber lid is rotated about an axis substantially perpendicular to the soil collar axis, can create a significant bluff body, causing assemblies analogous to assembly 10 to become unstable in windy conditions. When a measurement is initiated, the reverse order of steps just described is performed, with the chamber 70 being rotated directly above the sampling area and then gently lowered onto the soil collar 75.

The lift-and-rotate mechanism minimizes the footprint of the mechanical mechanism used for chamber 70 movement. The simplicity of the core mechanism allows for a minimal number of moving parts, thus significantly reducing both the material and manufacturing costs. The entire mechanism is enclosed in the weather-tight enclosure 150, preferably using static sealing design. The enclosure 150 preferably has only a single dynamic penetration, which is sealed against the elements using a rod-wiper/seal combination popular in hydraulic-cylinder actuator applications.

At the core of the lift-and-rotate mechanism in this preferred embodiment is a simple mechanism that converts the rotary motion of an electric motor to first a translational, and then rotational motion. The operating principle behind the lift-and-rotate mechanism is illustrated schematically in FIGS. 4A-4D, which illustrate the operating principle using a linear motion analogy. Once the linear motion analogy is understood, the translation to rotary motion is straightforward. Consider two slots 200, 210 cut into two different plates. Suppose that these plates are constrained to each other so that they may slide relative to each other right and left, but they may not slide up and down. Further, assume that a pin 220 passes through both slots 200, 210. Geometrically, the pin 220 can be thought of as the intersection point of the two slots 200, 210. For illustration, assume slot 210 is fixed, and slot 200 can translate left-to-right with respect to slot 210. Starting with FIG. 4A, assume that slot 200 begins to move toward the right. The motion of slot 200 moves the intersection point of the two slots 200, 210, and the pin 220 subsequently follows. The pin 220 will move to the right in slot 210 until it can no longer do so (see FIG. 4B). When the pin 220 enters the vertical portion of slot 210, it can no longer move to the right. Meanwhile, slot 200 continues to translate to the right, and the intersection point of the two slots 200, 210 continues upward. The pin 220, constrained in both slots 200, 210, subsequently moves upward also (see FIG. 4C). Finally, as slot 200 continues to move to the right, the pin 220 reaches the top of slot 210 (see FIG. 4D). The pin 220 can be lowered and returned to its starting position by reversing the steps just described. The unique intersection point of the two slots 200, 210 creates a reversible mechanism with a single-valued state. The single-valued state of the mechanism simplifies the control of the mechanism since the location of the pin 220 within the L-shaped slot 210 completely defines the state of all moving components of the mechanism.

Figures 4A, 4B, 4C, 4D:
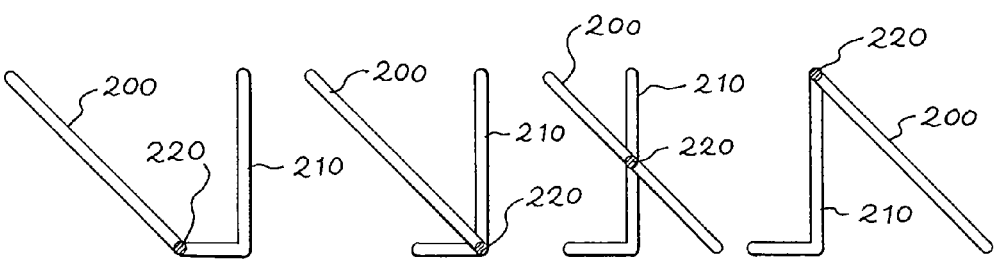
FIGS. 4A-4D are illustrations of conceptual linear slot geometry analogous to that used to create lift and rotate motion of a preferred embodiment.

If one considers only the motion of the pin 220 from left to right in FIG. 4A, it first translates horizontally within slot 200, moving at exactly the same speed as slot 200. When the pin 220 encounters the turn in slot 210, it begins to rise vertically within slot 210. Note that the pin's 220 speed during the vertical rise is no longer the same speed as slot 200 but is rather a function of the speed of slot 200 along with the slope of slot 200. Sloping slot 200 further toward the horizontal produces slower rise speeds while slopes nearer the vertical produce faster rise speeds.

Figure 5:
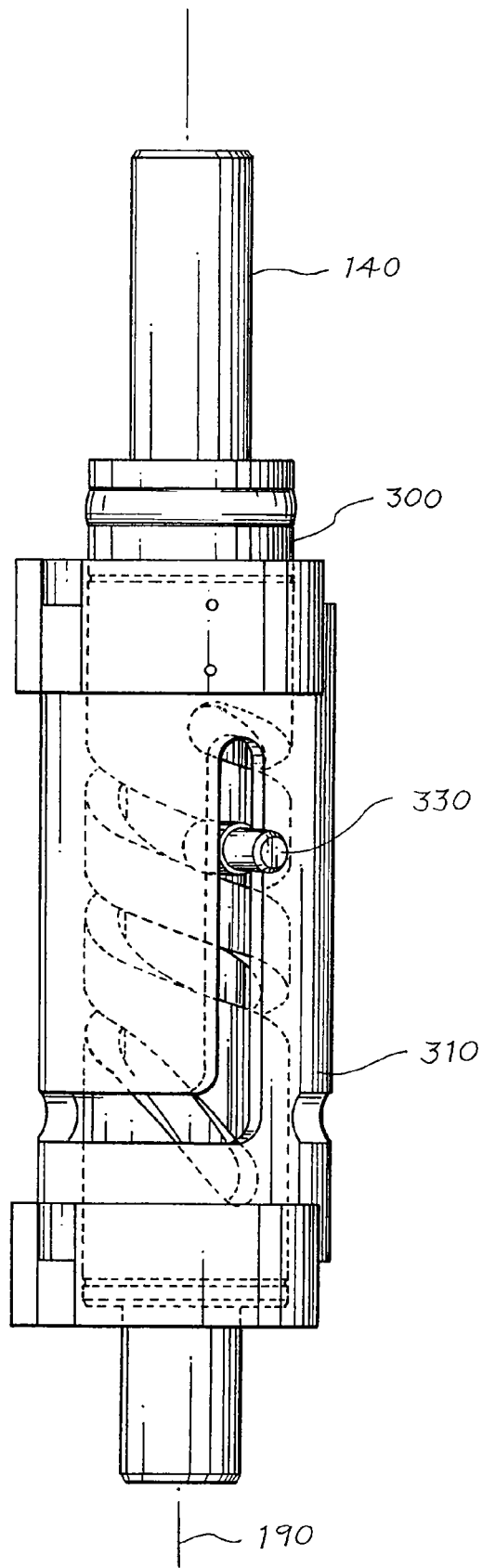
FIG. 5 is an illustration of a preferred embodiment in which the slots shown in FIGS. 4A-4D are wrapped around concentric cylinders.

In the implementation of this presently preferred embodiment, the sloped slots 200, 210 in FIGS. 4A-4D are wrapped around two concentric cylinders 300, 310 (see FIG. 5). Thus, slot 200 becomes a helical slot in annular cylinder 300, and slot 210 becomes an L-shaped slot in annular cylinder 310. In FIG. 5, the L-shaped slot is formed in the translucent exterior annular cylinder 310, and the helical slot is formed on the interior annular cylinder 300. Both slotted cylinders 300, 310 are allowed to rotate with respect to one another and with respect to the interior column 140, which contains the rotational axis 190 (see FIGS. 2 and 3). The slotted cylinders 300, 310 cannot translate with respect to one another but can both rotate and translate relative to the interior column 140. In the presently preferred embodiment shown in FIG. 5, a pin 330 is fixed rigidly to the interior column 140, which is stationary. The motion of the chamber 70 is rigidly coupled to the outermost cylinder 310 with the L-shaped slot. It is clear that the chamber 70 can rotate about axis 90 when the pin 330 is in the horizontal portion of the L-shaped slot and can translate vertically when the pin 330 is in the vertical portion of the L-shaped slot. Rotation of the cylinder 300 with the helical slot with respect to cylinder 310 causes the overall chamber 70 motion.

It should be noted that the slope of slot 200 in FIGS. 4A-4D, which translates into a helical slot in FIG. 5, controls not only the speed of the lift but also a mechanical force advantage in the raising and lowering of the chamber 70. In FIGS. 4A-4D, for a given horizontal force on slot 200, a vertical force is applied either upward or downward on the pin 220 depending on the direction of motion. Thus, slopes nearer the horizontal will provide higher vertical forces on the pin 200. In fact, the preferred embodiment shown in FIG. 5 uses two different slopes on the helical slot. The more gradual slope provides for mechanical advantage during the raising and lowering of the cylinder 300, and also reduces the speed of chamber 70 descent when closing the chamber 70. Slowing the chamber 70 descent speed is preferred to minimize soil and pressure disturbances above the soil prior to a flux measurement.

Figure 6:
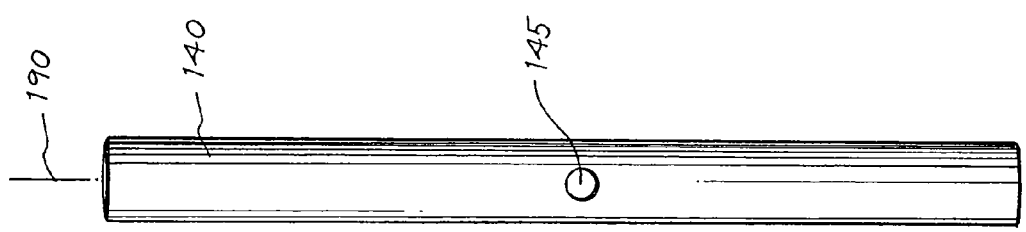
FIG. 6 is an illustration of an interior column of a lift-and-rotate mechanism of a preferred embodiment.

Returning to the drawings FIGS. 6-10 are illustrations showing the assembly of a lift-and-rotate mechanism 400 of a preferred embodiment. With reference to FIG. 6, the assembly starts with an interior column 140 (which is also referred to herein as a vertical shaft). The interior column 140 comprises the single vertical axis of rotation 190 for the lift-and-rotate motion. The interior column 140 also comprises a a single horizontal hole 145, which serves as an attachment point for the main drive pin 330, which is described below. In a presently preferred embodiment, the interior column 140 is made of anodized aluminum, is 11 inches in length, and has an outer diameter of one inch. Also, the hole 145 is preferably 5.3 inches from the bottom of the interior column 140.

Figure 7:
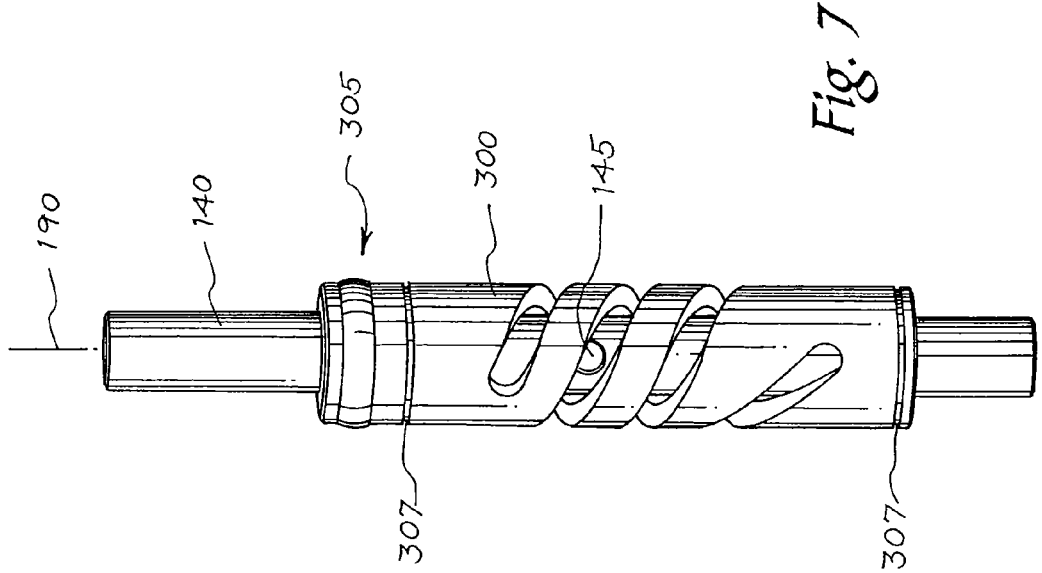
FIG. 7 is an illustration of a mid column installed around an interior column of a lift-and-rotate mechanism of a preferred embodiment.

In FIG. 7, a mid column 300 is installed around the interior column 140. The mid column 300 is an annular cylinder with a helical slot and is slid onto the interior column 140. The helical slot of the mid column 300 passes completely through the mid column 300, allowing a pin of appropriate diameter to be inserted completely through. The mid column 300 preferably has plastic sleeve bushings mounted to the interior diameter at either end. At the stage of assembly shown in FIG. 7, the mid column 300 can both rotate and translate up-and-down on the interior column 140. Near the top of the mid column 300 is a crowned area 305, which will serve as one of the pulleys in a belt drive mechanism. Incorporation of the pulley geometry into the mid column 300 reduces the part count and requires less assembly time than a separate drive pulley. Both ends of the mid column 300 contain grooves 307 which, when fitted with snap rings, will couple vertical loads to an outer column 310 (see FIG. 8).

The mid column 300 contains a segmented helical slot with two different lead angles of 20 and 45 degrees. The 20-degree lead angle is engaged during the lift phase of the motion, and the 45-degree lead angle is engaged during the rotate phase of the motion. The gentler 20-degree lead angle provides more lifting force during the lift phase of the motion than a steeper lead angle. However, lead angles shallower than 20-degrees may become problematic since there is preferably some minimum amount of material thickness between slots to maintain structural integrity of the mid column 300. The width of the slot remains constant to accept the main drive pin 330. In a presently preferred embodiment, 20-degrees is seen as the shallowest lead angle that can be achieved without degrading the structural integrity of the mid column 300. Also in a presently preferred embodiment, the mid column 300 is 7 inches in length and has an outer diameter of 1.75 inches (with an inner diameter that closely matches the outer diameter of the inner column 140). The slot width of the mid column 300 is preferably 0.4 inches.

Figure 8:
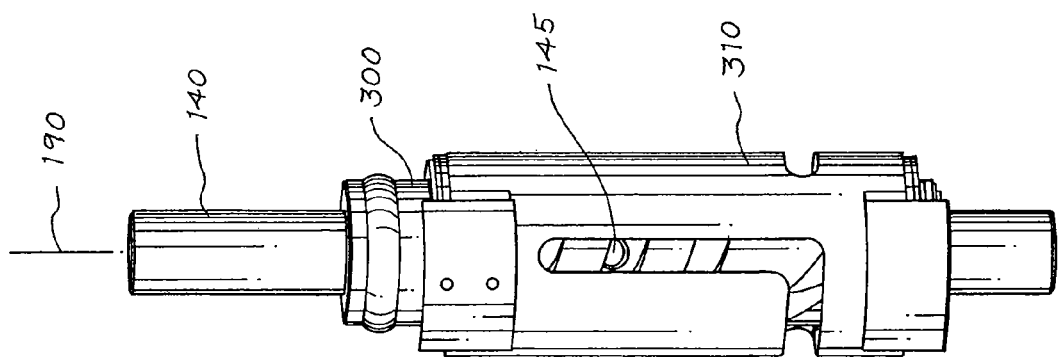
FIG. 8 is an illustration of an outer column installed over a mid column/interior column assembly of a lift-and-rotate mechanism of a preferred embodiment.

FIG. 8 is an illustration of an outer column 310 installed over the mid column 300. The outer column 310 can be slid onto the mid column 300. The outer column 310 is an annular cylinder with an L-shaped slot, with the L-shaped slot passing completely through the outer column 310. The L-shaped slot of the outer column 310 has both vertical and horizontal legs. Once the outer column 310 is slid into place, it is vertically constrained to the mid column 300 using flanged bushings (preferably, Igus), thrust washers, and snap rings, which fit into grooves of the mid column 300. At the stage of assembly shown in FIG. 8, the outer column 310 can rotate with respect to the mid column 300 but cannot translate vertically with respect to the mid column 300, and the mid column 300 and outer column 310 translate together. Also at this stage of assembly, the mid column 300 can rotate with respect to the interior column 140, and the mid column 300 and outer column 310 together can translate relative to the interior column 140. It is preferred that flange bushings be mounted in the inside diameter of the outer column 310, along with thrust washers and snap rings. These components are used to translate vertical forces from the mid column 300 to the outer column 310 while not impeding relative motion.

In a presently preferred embodiment, the outer column 310 has a length of 6.3 inches and an outer diameter of 2.5 inches. The vertical slot in the outer column 310 is preferably 3 inches (this allows for a three-inch vertical lift), and the horizontal slot is preferably 2.5 inches (this allows a 120-degree rotation).

Figure 9:
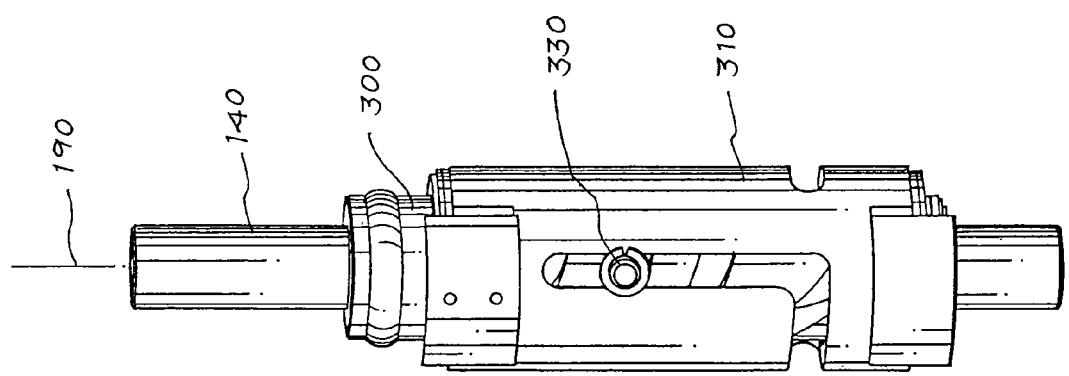
FIG. 9 is an illustration of a drive column assembly of a lift-and-rotate mechanism of a preferred embodiment.

The assembly in FIG. 8 is then secured together with a single drive pin 330, as shown in FIG. 9. This drive pin 330 passes completely through the L-shaped slot in the outer column 310, the helical slot in the mid column 300, and the single hole 145 in the interior column 140. The drive pin 330 thus uniquely locates the mid column 300 and outer column 310 with respect to the horizontal hole 145 in the interior column 140. The pin 330 is secured in place using two snap rings, which fit into grooves on either end of the pin 330.

In a presently preferred embodiment, the drive pin 330 is a 0.375 inches hardened steel pin (with a Rockwell C hardness of 63-65) and has two grooves, each 0.029 inches wide. Also, the outer diameter of the snap rings is preferably 0.61 inches. The mid column 300 and outer column 310 are hard-coat anodized with an impregnated PTFE (Nituff™ coating from Nimet Industries, Inc. in South Bend, Ind.). The exterior of the pin 330 and the interior of the grooves in both the mid column 300 and outer column 310 are wear surfaces since the pin 330 rides in the slots of the columns 300, 310. The initial intent is to use the Nituff™ coating and unlubricated components to eliminate the need for periodic lubrication. Should this prove infeasible, the main drive pin 330 and the slots of the mid column 300 and outer column 310 can be lubricated to reduce friction and noise that may result from sliding contact.

If the interior column 140 in FIG. 9 is held fixed, the assembly of the mid column 300 and outer column 310 is constrained to translate up-and-down when the drive pin 330 is in the vertical leg of the outer column 310 slot. Similarly, the outer column 310 is constrained to rotate about the interior column 140 and mid column 300 when the drive pin 330 is in the horizontal leg of the outer column 310 slot. Rotation of the mid column 300 with respect to the outer column 310 causes the drive pin 330 to move throughout the L-shaped slot of the outer column 310. Thus, aside from motorization, the core components of the lift-and-rotate mechanism 400 are now present in FIG. 9.

FIG. 10 shows the assembly of FIG. 9 with the addition of a DC gear-motor 350 and belt drive mechanism. The DC motor 350 is rigidly attached to the outer column 310 via a motor mounting plate 370, and a flat drive belt 360 connects the integrated crowned pulley 305 on the mid column 300 to a motor-mounted pulley 380. The motor 350 causes a relative rotation of the mid column 300 with respect to the outer column 310. During the lift phase of the motion, the mid column 300 rotates with respect to the outer column 310, and the outer column 310 translates vertically along with the mid column 300 with respect to the inner column 140. During the rotate phase of the motion, the mid column 300 remains stationary with respect to the inner column 140, and the outer column 310 rotates with respect to the inner column 140 and mid column 300. Referring back to FIG. 1, the chamber support structure 100 is rigidly coupled to the outer column 310. Thus, the lift-and-rotate motion of the outer column 310 is directly transferred to the chamber 70 through the chamber support structure 100.

In a presently preferred embodiment, the belt 360 is flat with 95-97% efficiency, made of polyethylene, and has a width of 0.25 inches and a length of 7.8 inches. A suitable belt can be purchased from SDP-SI. If a flat belt slips prematurely during the transition from lift to rotate motions, alternative flat belt drive geometries can be used. Alternative mechanisms can also be used, such as a chain-drive mechanism (two sprockets and a single chain) and a v-belt drive mechanism. Preferably, the pulley on the mid column 310 has a diameter of 1.75 inches, and the pulley coupled with the motor 350 has a diameter of 0.715 inches. Also in the presently preferred embodiment, the motor 350 has a gear ratio of 585:1. Suitable brushed DC gear motors can be purchased from Micromo, Pittman, and Globe.

By way of summary, the presently preferred embodiment described above incorporates the following features that are useful in maintaining low cost and reduced complexity of the lift-and-rotate mechanism while providing much of the same functionality as the more complex LI-8100 Long-Term Chamber:

(1) The lift-and-rotate motion concept allows all of the moving components to be designed around a single vertical axis, offset horizontally from the sampling area. The mechanism necessary to produce the motion can be compactly designed around this vertical axis. In contrast, in the LI-8100 Long Term Chamber, motion is driven around two horizontal axes. The first horizontal axis is responsible for the bulk translation of the chamber to and from the sampling area, and the second horizontal axis is responsible for rotation of the chamber to maintain a downward facing orientation. The motions of these two axes are kinematically coupled through a drive chain. The lift-and-rotate concept allows all of the motion to occur about a single axis; namely, a single vertical axis. The single axis reduces the complexity of kinematically coupling multiple axes. The vertical nature of the axis allows the mechanism to have a minimal footprint on surrounding soil.

(2) The concentric column design decouples the lift phase and the rotate phase of the motion and allows the use of a rotary-gear motor. When contrasted with the linear lead-screw alternative described below, the concentric column design reduces the vertical height of the actuating mechanism by more than 40%.

(3) The concentric cylinder design allows both the lift and rotate phases of the motion to be accomplished by a single motor driven at constant speed. The speed of the lift phase can be controlled both through the motor speed, the pulley size ratios, and the helical lead angle of the mid-drive column. The speed of the rotate phase is controlled only by the motor speed and the pulley size ratios. Thus, the designer can choose the rotate speed by selecting a motor speed and pulley size ratio and can then tune the lift speed by varying the helical lead angle. There is a tradeoff with mechanical advantage, as steeper helical lead angles increase the lift speed but subsequently decrease the lift force for a given motor torque. The presently preferred embodiment uses a helical lead angle of 20 degrees for the lift phase and a helical lead angle of 45 degrees for the rotate phase.

(4) A compliant coupling between the chamber and the chamber support structure allows nearly the same sealing force to be applied to the chamber for a range of positions of the support structure. This allows simple end-point positional on-off control of the lift-and rotate mechanism while maintaining nearly a constant sealing force at the chamber. Conversely, a rigid chamber support structure would require precise positional control of the lift-and-rotate mechanism in order to maintain a constant downward sealing force at the chamber.

(5) The end-point on-off positional control is preferably accomplished using two Hall-effect limit switches located at either end of travel. When an open command is received from a master controller, the motor is driven in the open direction at constant speed until a limit switch is reached. Similarly, when a close command is received from a master controller, the motor is driven in the close direction at constant speed until the closed limit switch is reached. The limit switch function could be similarly accomplished with mechanical switches, optical interrupt switches, or Hall-effect switches. The design uses Hall-effect interrupt switches (preferably, a Honeywell SR17C-J6 switch) to provide a lifetime far beyond that of mechanical switches while avoiding the dust/contamination sensitivity of optical interrupt switches.

(6) The vertical and rotational loads are transferred from the two slotted drive columns to a single drive pin. The design uses a lubricated pin in sliding contact with the mating slots. The sliding-contact design eliminates the need for rolling contact bearings or bushings, subsequently reducing system complexity and cost.

(7) The concentric drive cylinder design allows for the use of small plastic bushings (preferably from Igus, East Providence, R.I.), which are less expensive and more debris tolerant than conventional ball bearings. Moreover, the plastic bushings can provide for both radial and thrust loads like a ball bearing without the complexity and cost of the ball bearing. The use of bushings rather than bearings further reduces the size of the mechanism since rolling-element bearings have larger outside diameters than a bushing for the same inside diameter.

(8) The use of a belt coupling between the drive motor and the mid column allows the mechanism to slip should the chamber or chamber support structure come into contact with an obstacle. The slip is a self-protection mechanism that prevents damage to the device or external object should a significant obstacle be encountered. The point at which the belt slips can be coarsely adjusted (during manufacture) by varying the belt tension. Self protection is also incorporated by monitoring the drive motor electrical current and shutting off motor current should it exceed a predefined value.

There are several alternatives that can be used with these embodiments. For example, in the embodiment shown in FIG. 1, the height of the cylindrical enclosure 150 exceeds the height of the sampling chamber 70, which can negatively affect the vent 90. The sampling chamber 70 is equipped with a vent 90 to allow pressure equalization between the interior and exterior of the chamber 70. The vent mechanism 90 relies on certain air-flow patterns to function as designed. If the cylindrical enclosure 150 has an impact on air-flow patterns around the vent 90 (e.g., if the cylindrical enclosure 150 produces non-uniformities in air-flow that may adversely affect the vent's 90 capability to equalize pressure inside and outside the chamber 70), the height of the cylindrical enclosure 150 can be reduced or the vent 90 can be relocated to a less affected area.

Also, in the embodiment shown in FIG. 1, cables (e.g., electrical signal and power cables) are routed to the lifting-and-rotating cylindrical enclosure 150. Accordingly, these cables are lifted and rotated with the mechanism. If the cables catch and bind on surrounding objects during chamber motion, a track or enclosure can be used to manage the cables to remove the potential for catching and binding. Further, instead of using a DC motor, other mechanisms can be used, including, but not limited to, pneumatic bellows and hydraulics. Further, instead of using a single motor to perform both the translational and rotational moving, two motors can by used—one for each type of movement.

The preferred embodiment described above uses a fixed-pin geometry, and the primary lift-and rotate mechanism along with circuit boards, the enclosure, motor, etc are all moved up and down around the main drive pin. While this geometry may be the easiest geometry to seal, an alternative geometry based on the same mechanical principal can be used. In this alternative, the rotating cylinders are fixed, and the interior shaft is allowed to perform the rotation and lift. This alternative would eliminate the moving cables issue described above. Further, this alternative would reduce the moving mass of the system, thereby decreasing the torque requirements for the motor and improving overall mechanical efficiency. For these reasons, it may be preferred to use this fixed-cylinder-geometry alternative over translating/rotating cylinder geometry described above.

In another alternative, a linear actuator is used instead of using the rotational gear-motor described above. (As discussed above, a sprocket/chain drive mechanism and a v-belt mechanism can be used.) Examples of commercial off-the-shelf linear actuators are the Hybrid Linear Actuator, Size 23 External 57000 Series and the Hybrid Linear Actuator, Size 17 External 43000 Series from Haydon Switch and Instrument (HSI), Waterbury, Conn. (USA). A linear actuator comprises a lead screw integrated with a lead nut and a motor. The linear actuators from HSI mentioned above utilize stepper motors rather than brushed DC motors. In operation, the linear actuator would be vertically mounted in a vertical annular cylinder, with the axis of the cylinder and the axis of the lead screw being concentric. The cylinder would have two diametrically opposed slots through which a horizontal pin would pass, from one side of the cylinder through the opposing side. This pin would be rigidly attached to the lead nut of the motor and would be constrained to move in the slots cut in the cylinder. The slots would have a vertical portion which accomplishes the lift phase of the lift-and-rotate motion. Thus, the motor would lift the pin vertically in the slot, and this pin motion would be directly transferred to the chamber.

The rotate phase of the motion is accomplished by turning the vertical slot, after a prescribed lift distance, into a helical slot about the cylinder's axis. The helical slot would cause the pin to rotate about the cylinder axis as it translated vertically, being pushed or pulled by the linear actuator. A large helical lead angle would cause the pin to rotate slowly during an upward or downward translation. A smaller helical lead angle would cause a larger rotation for the same translation. There are also mechanical-advantage considerations when selecting an appropriate lead angle.

An advantage of this alternative is that half of the mechanism could be purchased as an assembly directly from HSI. There are significant cost savings to the purchase of this integrated assembly versus purchasing component parts. However, in this alternative, vertical translation achieves the rotate phase. Without vertical translation, there is no mechanism to achieve rotation here. Helical lead angles near 45 degrees can be used for speed and mechanical advantage. However, at these helical lead angles, the mechanism may become very tall. Since the height of the mechanism can potentially shade the sampling area, drive size and weight, and potentially interfere with air-flow patterns around the chamber vent, the rotational gear-motor embodiment described above is preferred. By using a rotational gear-motor instead of a linear actuator, the preferred embodiment described above allows a decoupling between the lift phase and rotate phase of the motion. The rotate phase no longer requires the vertical translation required in the linear actuator alternative. Thus, the preferred embodiment described above minimizes the height of the drive column by decoupling the lift phase and rotate phase and accomplishes both motions with only a single drive motor running at constant speed.

Finally, it should be noted that the term "lift-and-rotate mechanism" is being used herein to refer to any suitable assembly that can lift and rotate the chamber. The term "lift-and-rotate mechanism" in the claims should not be limited to the specific designs shown and described in these embodiments and is not intended to be a "means-plus-function" clause under 35 U.S.C. §112, paragraph 6.

It is intended that the foregoing detailed description be understood as an illustration of selected forms that the invention can take and not as a definition of the invention. It is only the following claims, including all equivalents, that are intended to define the scope of this invention.

What is claimed is:

1. A gas flux chamber assembly comprising:
   a soil collar;
   a chamber; and
   a lift-and-rotate mechanism coupled with the chamber and comprising a rotational axis substantially parallel to the soil collar, wherein the lift-and-rotate mechanism is operative to move the chamber between first and second positions, wherein the chamber is positioned on the soil collar in the first position and is positioned outside of an area above the soil collar in the second position, wherein the lift-and-rotate mechanism moves the chamber from the first position to the second position by lifting the chamber off of the soil collar and then rotating the chamber, about the rotational axis, outside of the area above the soil collar.

2. The invention of claim 1, wherein the lift-and-rotate mechanism comprises:
   a first cylindrical column comprising a hole;
   a second annular cylindrical column installed around the first cylindrical column, wherein the second cylindrical column comprises a helical slot;
   a third annular cylindrical column installed around the second cylindrical column, the third cylindrical column comprising an L-shaped slot; and
   a pin passing through the L-shaped slot, helical slot, and hole.

3. The invention of claim 2, wherein the helical slot comprises two different lead angles, one of which is engaged by the pin during lift, and the other of which is engaged during rotation.

4. The invention of claim 2, wherein the second annular cylindrical column comprises a first pulley, and wherein the lift-and-rotate mechanism further comprises:
   a motor;
   a second pulley coupled with the motor; and
   a belt coupling the first pulley and the second pulley.

5. The invention of claim 2, wherein the second and third annular cylindrical columns are fixed during lift and rotate motions and the first cylindrical column performs the lift and rotate motions.

6. The invention of claim 2, wherein the first cylindrical column is fixed during lift and rotate motions and the second and third annular cylindrical columns perform the lift and rotate motions.

7. The invention of claim 1, wherein the lift-and-rotate mechanism comprises a linear actuator and a cylinder with a helical slot.

8. The invention of claim 1 further comprising:
   a spring disk coupled with the chamber;
   a chamber support structure coupled with the lift-and-rotate mechanism; and
   a plurality of springs coupling the spring disk with the chamber support structure.

9. The invention of claim 1 further comprising a collar seal located between the soil collar and the chamber when the chamber is in the first position.

10. The invention of claim 1, wherein the lift-and-rotate mechanism comprises pneumatic actuation.

11. The invention of claim 1, wherein the lift-and-rotate mechanism comprises hydraulic actuation.

12. The invention of claim 1, wherein the lift-and-rotate mechanism comprises a chain drive.

13. The invention of claim 1, wherein the lift-and-rotate mechanism comprises a v-belt drive.

14. A gas flux chamber assembly comprising:
    a soil collar;
    a chamber; and
    means for moving the chamber from a first position where the chamber is positioned on the soil collar to a second position where the chamber is positioned outside of an area above the soil collar by lifting the chamber off of the soil collar and then rotating the chamber about a rotational axis substantially parallel to the soil collar outside of the area above the soil collar.

15. The invention of claim 14, wherein the means for moving comprises a lift-and-rotate mechanism.

16. The invention of claim 15, wherein the means for moving comprises:
    a first cylindrical column comprising a hole;
    a second annular cylindrical column installed around the first cylindrical column, wherein the second cylindrical column comprises a helical slot;
    a third annular cylindrical column installed around the second cylindrical column, the third cylindrical column comprising an L-shaped slot; and
    a pin passing through the L-shaped slot, helical slot, and hole.

17. The invention of claim 16, wherein the helical slot comprises two different lead angles, one of which is engaged by the pin during lift, and the other of which is engaged during rotation.

18. The invention of claim 16, wherein the second annular cylindrical column comprises a first pulley, and wherein the means for moving further comprises:
   a motor;
   a second pulley coupled with the motor; and
   a belt coupling the first pulley and the second pulley.

19. The invention of claim 16, wherein the second and third annular cylindrical columns are fixed during lift and rotate motions and the first cylindrical column performs the lift and rotate motions.

20. The invention of claim 16, wherein the first cylindrical column is fixed during lift and rotate motions and the second and third annular cylindrical columns perform the lift and rotate motions.

21. The invention of claim 14, wherein the means for moving comprises a linear actuator and a cylinder with a helical slot.

22. The invention of claim 14 further comprising:
   a spring disk coupled with the chamber;
   a chamber support structure coupled with the means for moving; and
   a plurality of springs coupling the spring disk with the chamber support structure.

23. The invention of claim 14 further comprising a collar seal located between the soil collar and the chamber when the chamber is in the first position.

24. The invention of claim 14, wherein the means for moving comprises pneumatic actuation.

25. The invention of claim 14, wherein the means for moving comprises hydraulic actuation.

26. The invention of claim 14, wherein the means for moving comprises a chain drive.

27. The invention of claim 14, wherein the means for moving comprises a v-belt drive.

28. A method for use with a gas flux chamber assembly comprising a soil collar and a chamber, the method comprising:
   (a) providing a gas flux chamber assembly comprising a soil collar and a chamber with the chamber positioned on the soil collar;
   (b) lifting the chamber off of the soil collar; and
   (c) rotating the chamber, about a rotational axis substantially parallel to the soil collar, outside of an area above the soil collar.

29. The invention of claim 28, wherein (b) and (c) are performed by a lift-and-rotate mechanism.

30. The invention of claim 29, wherein the lift-and-rotate mechanism comprises:
   a first cylindrical column comprising a hole;
   a second annular cylindrical column installed around the first cylindrical column, wherein the second cylindrical column comprises a helical slot;
   a third annular cylindrical column installed around the second cylindrical column, the third cylindrical column comprising an L-shaped slot; and
   a pin passing through the L-shaped slot, helical slot, and hole.

31. The invention of claim 30, wherein the helical slot comprises two different lead angles, one of which is engaged by the pin during lift, and the other of which is engaged during rotation.

32. The invention of claim 30, wherein the second annular cylindrical column comprises a first pulley, and wherein the lift-and-rotate mechanism further comprises:
   a motor;
   a second pulley coupled with the motor; and
   a belt coupling the first pulley and the second pulley.

33. The invention of claim 30, wherein the second and third annular cylindrical columns are fixed during (b) and (c), and wherein the first cylindrical column performs (b) and (c).

34. The invention of claim 30, wherein the first cylindrical column is fixed during (b) and (c), and wherein the second and third annular cylindrical columns perform (b) and (c).

35. The invention of claim 29, wherein the lift-and-rotate mechanism comprises a linear actuator and a cylinder with a helical slot.

36. The invention of claim 29, wherein the gas flux chamber assembly further comprises:
   a spring disk coupled with the chamber;
   a chamber support structure coupled with the lift-and-rotate mechanism; and
   a plurality of springs coupling the spring disk with the chamber support structure.

37. The invention of claim 29, wherein the lift-and-rotate mechanism comprises pneumatic actuation.

38. The invention of claim 29, wherein the lift-and-rotate mechanism comprises hydraulic actuation.

39. The invention of 29, wherein the lift-and-rotate mechanism comprises a chain drive.

40. The invention of claim 29, wherein the lift-and-rotate mechanism comprises a v-belt drive.

41. The invention of claim 28, wherein the gas flux chamber assembly further comprises a collar seal located between the soil collar and the chamber when the chamber is on the soil collar.

* * * * *